(12) United States Patent
Das et al.

(10) Patent No.: US 11,452,790 B2
(45) Date of Patent: Sep. 27, 2022

(54) AIR FRESHENING FORMULATION

(71) Applicant: Reckitt Benckiser (Brands) Limited, Slough (GB)

(72) Inventors: Avijit Das, Haryana (IN); Scott Rudkin, Hull (GB); Anne Szklarz, Hull (GB)

(73) Assignee: Reckitt Benckiser (Brands) Limited, Slough (GB)

( * ) Notice: Subject to any disclaimer, the term of this patent is extended or adjusted under 35 U.S.C. 154(b) by 702 days.

(21) Appl. No.: 16/315,487

(22) PCT Filed: Jun. 22, 2017

(86) PCT No.: PCT/GB2017/051832
§ 371 (c)(1),
(2) Date: Jan. 4, 2019

(87) PCT Pub. No.: WO2018/007785
PCT Pub. Date: Jan. 11, 2018

(65) Prior Publication Data
US 2019/0298878 A1 Oct. 3, 2019

(30) Foreign Application Priority Data
Jul. 6, 2016 (GB) ..................................... 1611760

(51) Int. Cl.
*A61L 9/14* (2006.01)
*A61L 9/01* (2006.01)
(52) U.S. Cl.
CPC ...... *A61L 9/14* (2013.01); *A61L 9/01* (2013.01); *A61L 2209/133* (2013.01)
(58) Field of Classification Search
CPC ......... A61L 9/01; A61L 9/14; A61L 2209/133
See application file for complete search history.

(56) References Cited

U.S. PATENT DOCUMENTS

| | | | |
|---|---|---|---|
| 4,810,690 A | 3/1989 | Dumas | |
| 6,290,945 B1 | 9/2001 | Baker et al. | |
| 6,506,723 B1 | 1/2003 | Walsum et al. | |
| 2010/0099594 A1* | 4/2010 | Bobnock | A61K 8/8129 510/513 |
| 2013/0090283 A1* | 4/2013 | Guy | A61L 9/14 512/2 |
| 2013/0336914 A1* | 12/2013 | Horenziak | C11D 3/26 424/76.1 |
| 2014/0048617 A1* | 2/2014 | Furner | B65D 83/285 239/55 |
| 2014/0162932 A1* | 6/2014 | Hatakeyama | C11B 9/00 512/2 |
| 2017/0274110 A1* | 9/2017 | Nwachukwu | A61L 9/04 |
| 2017/0274111 A1* | 9/2017 | Nwachukwu | A61L 9/01 |

FOREIGN PATENT DOCUMENTS

| | | |
|---|---|---|
| AU | 2001228669 B2 | 8/2001 |
| AU | 2011286597 B2 | 2/2012 |
| CN | 104524615 A | 4/2015 |
| EP | 0462605 A2 | 6/1991 |
| EP | 0520547 A2 | 6/1992 |
| WO | 2011138620 A1 | 5/2011 |
| WO | 2015148894 A1 | 3/2015 |

OTHER PUBLICATIONS

English Language Machine Translation of CN104524615 (Year: 2015).*
IN Examination Report in corresponding application IN 201947004269 dated Jan. 20, 2021.
AU Examination Report in corresponding application AU 2017294133 dated Jul. 16, 2021.
International Search Report and Written Opinion of the International Searching Authority for corresponding application PCT/GB2017/051832 dated Aug. 11, 2017.
GB Search Report for corresponding application GB1611760.8 dated Dec. 20, 2016.

* cited by examiner

*Primary Examiner* — Sean E Conley
(74) *Attorney, Agent, or Firm* — Norris McLaughlin PA

(57) ABSTRACT

The invention relates to an air freshening formulation. The air freshening formulation is particularly suitable for use as an aerosol air freshening product. The aerosol products of the invention are also highly suitable for use in automatic aerosol dispensing devices.

26 Claims, No Drawings

AIR FRESHENING FORMULATION

BACKGROUND TO THE INVENTION

Air freshening products are widely used and come in a variety of forms. These include scented candles, wax melters, reed stick emanators, scented gels, liquid electrical plugins and aerosols. Of these aerosols are probably the most widely used air freshening product. The reason for their popularity no doubt stems from their ease of use (portable and requires no power source), rapid effect (the product is dispensed and dispersed immediately into the air), safety (no need for either electrical power or combustion) and simplicity.

Household aerosol products are generally divided into two classes, those that use LPG (liquid petroleum gas) propellants and those that use compressed gas (such as nitrogen) propellants.

LPG propellant aerosols are well known to offer better performance in terms of particle size and pressure profile.

Compressed gas propellant aerosols have well documented performance drawbacks, such as poor particle break up (large particle sizes), directionality (propellant does not mix with formulation) and pressure reduction over the lifetime of the product.

Despite these disadvantages, compressed gas propellants are increasingly used as they are both environmentally less damaging and less expensive.

The world market trend is also to move towards water-based aerosol formulations. This is due mainly to a regulatory issue; the reductions of the volatile organic content (VOC) levels in aerosol product has involved the reduction of the solvent level in many products and an increase of the water content.

Currently it is desirable to have a VOC propellant level of below 30% w/w not only to reduce cost but also to comply with increasingly stringent regulatory limits (e.g. a maximum of 24.5% w/w in the USA for air freshener products).

Increased water can give fall out problems and corrosion problems in standard tin-plate aerosol cans. EP2566525 A1 details a solution to this utilising a corrosion inhibitor and surfactant system.

However this solution has been found to cause problems, particularly in automatic aerosol dispensers. An example of which is Air Wick's® Freshmatic® device. This is because the surfactants are difficult to effectively aerosolise and cause build up gradually on the surfaces surrounding the dispenser.

It is one object of the present invention to solve this problem.

SUMMARY OF THE INVENTION

In a first aspect the invention provides an air freshening formulation comprising;
 a) water 30-65% by weight;
 b) alcohol 10-50% by weight;
 c) co-solvent 10-30% by weight;
 d) fragrance composition 0.1-15% by weight;
 wherein the air freshening composition comprises no surfactant.

In a second aspect the invention provides an aerosol canister comprising a formulation according to the first aspect of the invention and an aerosol propellant.

A third aspect of the invention provides a method of treating the air comprising the use of a canister according to the second aspect of the invention in an automatic aerosol dispensing device.

DESCRIPTION OF THE INVENTION

The applicants have found a highly effective aqueous air freshening composition. Preferably the composition is used as the basis of an air freshening aerosol formulation/product. The composition when used as an aerosol formulation provides excellent dispersion characteristics.

The composition does not produce a significant residue build-up when regularly sprayed over time in an automatic aerosol spraying device.

In its broadest the invention comprises an air freshening formulation with:
 a) water 30-65% by weight;
 b) alcohol 10-50% by weight;
 c) co-solvent 10-30% by weight;
 d) fragrance composition 0.1-15% by weight;
 and wherein the air freshening composition comprises no surfactant.

For the purposes of the present invention the terms "alcohol" and "co-solvent" are discrete, chemically distinct components to the inventive formulation. Additionally, for the purposes of the present invention the term "glycol ether" means any alkyl ethers of ethylene glycol or propylene glycol.

Additionally, for the purpose of the present invention the term "surfactant" means any amphiphilic compound that lower the surface tension (or interfacial tension) between two liquids or between a liquid and a solid. Surfactants may act as detergents, wetting agents, emulsifiers, foaming agents, and dispersants. Most commonly, surfactants are classified according to polar head group. A non-ionic surfactant has no charged groups in its head. The head of an ionic surfactant carries a net positive, or negative charge. If the charge is negative, the surfactant is more specifically called anionic; if the charge is positive, it is called cationic. If a surfactant contains a head with two oppositely charged groups, it is termed zwitterionic. The skilled person will be aware that there are a vast array of different chemical entities that fulfil these descriptions. The compositions of the present invention do not comprise any of these compounds.

Preferably the water comprises between 35 and 55%, and more preferably between 40 and 50% by weight of the formulation.

Preferably the alcohol comprises between 15 and 40%, and more preferably between 20 and 35% by weight of the formulation.

A particularly preferred alcohol may be selected from the group consisting of methanol, ethanol, propanol, isopropanol, butanol and mixtures thereof. In particularly preferred embodiments the solvent is ethanol.

The co-solvent may be any solvent miscible or partially miscible with water and/or the alcohol at normal conditions. It is preferred that the solvent be miscible with water under standard conditions.

Preferably the co-solvent comprises between 12 and 28% and more preferably between 15 and 25% by weight of the formulation.

Particularly preferred co-solvents include acetone, DMF (dimethylformamide), acetonitrile, diethyl ether, glycerol, MMB (3 methoxy 3 methyl 1 butanol), glycol ethers and mixtures thereof.

The glycol ether may comprise an ethylene glycol ether or a propylene glycol ether or a mixture of two or more ethylene or propylene glycol ethers.

Examples of suitable propylene glycol ethers include propylene glycol n-butyl ether (PnB), dipropylene glycol n-butyl ether (DPnB), dipropylene glycol methyl ether acetate (DPMA), tripropylene glycol methyl ether (TPM), propylene glycol methyl ether (PM) propylene glycol methyl ether acetate (PMA), dipropylene glycol methyl ether (DPM), and dipropylene glycol n-propyl ether (DPnP).

Examples of suitable ethylene glycol ethers include; ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, diethylene glycol monomethyl ether, diethylene glycol monoethyl ether, and diethylene glycol mono-n-butyl ether and mixtures thereof.

The glycol ether of the formulation may comprise a single ethylene or propylene glycol ethers or a mixture of two or more different glycol ethers.

A particularly preferred glycol ether used alone or in combination with others is dipropylene glycol n-propyl ether (DPnP).

Preferably the fragrance composition comprises between 1 and 6% by weight and more preferably between 1.5 and 4% by weight of the air freshening formulation. Any fragrance composition may be used with the present formulation.

In a particularly preferred formulation the alcohol is ethanol and the glycol ether is dipropylene glycol n-propyl ether (DPnP). Another preferred formulation comprises ethanol and MMB (3 methoxy 3 methyl 1 butanol). And another preferred formulation comprises ethanol and glycerol. Yet another preferred formulation comprises ethanol and acetone.

A particularly preferred air freshening formulation according to the present invention comprises;
  a) water 48-52% by weight;
  b) ethanol 26-30% by weight;
  c) dipropylene glycol n-propyl ether (DPnP) 18-22% by weight; and
  d) a fragrance composition 1-3% by weight The air freshening formulation may further comprise a corrosion inhibiter. Preferably the corrosion inhibitor, if included, comprises less than 0.5% by weight of the composition.

Particular examples of suitable corrosion inhibitors include borate salts.

The formulations of the present invention are preferably used as aerosol formulations/compositions. To achieve this the formulations are combined with one or more aerosol propellants and stored in a suitable canister.

The aerosol formulations may be prepared using any suitable aerosol propellant. The aerosol formulations may be prepared using a single propellant or a mixture of two or more different propellants.

Propellants for aerosols form two general classes,
  1) LPG propellants such as propane, n-butane, iso-butane dimethyl ether (DME) and methyl ethyl ether; and
  2) Compressed gas propellants such as nitrogen, carbon dioxide nitrous oxide and air.

In terms of performance small particle size and dispersion characteristics, generally LPG propellants are preferred. In terms of cost and environmental considerations, compressed gasses are generally preferred.

Aerosol compositions of the present invention are preferably compressed gas propellant aerosols, preferably nitrogen or air.

In a second aspect the present invention comprises an aerosol product comprising the formulation of the first aspect of the invention, at least one aerosol propellant and a suitable aerosol container or canister. For the purposes of the present invention the terms container and canister are interchangeable and have the same meaning.

The at least one propellant may be any propellant suitable in the art. Preferably the at least one aerosol propellant is a compressed gas propellant. And more preferably the at least one compressed gas propellant is selected from the group consisting of air, nitrogen and carbon dioxide.

Any suitable aerosol container or canister may be used. Preferably the container/canister will be selected from the group comprising, a steel canister, tin-plated steel canister or other corroding metal canister.

Preferably the volume ratio of propellant to formulation is propellant is within the range from 80:20 to 30:70, preferably from 70:30 to 50:50.

Preferably the initial flow rate of aerosol product from the canister is between 0.5 and 3.0 grams per second. The initial flow rate measured for the purposes of the present invention according the average release for the first 15 seconds of the product.

Preferably the mean particle size of the released aerosol is between 20 and 80 microns.

A particularly preferred use of the aerosol products of the present invention are in automatic aerosol dispensing devices.

A good example of which is the Freshmatic® product from Air Wick®. These products enable the constant, steady release of aerosol over weeks and months by activating the aerosol canister to release the fragrance formulation every few mins.

The aerosol products of the present invention have excellent fragrance parameters while having no residue problems when used in automatic spray devices.

The invention claimed is:

1. An air freshening formulation present within a pressurizable canister comprising a propellant, the air freshening formulation comprising;
  a) water, 30-65% weight %;
  b) alcohol, 10-50 weight %;
  c) co-solvent, 10-30 weight %, selected from the group consisting of: acetone, dimethylformamide, acetonitrile, diethyl ether, glycerol, propylene glycol n-butyl ether, dipropylene glycol n-butyl ether, dipropylene glycol methyl ether, tripropylene glycol methyl ether, dipropylene glycol methyl ether acetate, propylene glycol, dipropylene glycol n-propyl ether, ethylene glycol monopropyl ether, ethylene glycol monoisopropyl ether, ethylene glycol monobutyl ether, ethylene glycol monophenyl ether, ethylene glycol monobenzyl ether, diethylene glycol monomethyl ether, diethylene glycol monomethyl ether, diethylene glycol mono-n-butyl ether and mixtures thereof;
  fragrance composition, 0.1-15 weight %;
  and wherein the air freshening formulation comprises no surfactant.

2. The air freshening formulation according to claim 1 wherein the water comprises between 35 and 55% by weight of the formulation.

3. The air freshening formulation according to claim 1, wherein the alcohol comprises between 15 and 40% by weight of the formulation.

4. The air freshening formulation according to claim 1, wherein the co-solvent comprises between 12 and 28% by weight of the formulation.

5. The air freshening formulation according to claim 1, wherein the fragrance composition comprises between 1 and 6% by weight of the formulation.

6. The air freshening formulation according to claim 1, wherein the alcohol is selected from the group consisting of: methanol, ethanol, propanol, isopropanol, butanol and mixtures thereof.

7. The air freshening formulation according to claim 6 wherein the alcohol is ethanol.

8. The air freshening formulation according to claim 1, wherein the co-solvent is selected from the group consisting of: acetone, dimethyl formamide, acetonitrile, diethyl ether, glycerol, and mixtures thereof.

9. The air freshening formulation of claim 1 wherein the co-solvent is selected from the group consisting of: propylene glycol n-butyl ether (PnB), dipropylene glycol n-butyl ether (DPnB), dipropylene glycol methyl ether acetate (DPMA), tripropylene glycol methyl ether (TPM), propylene glycol methyl ether acetate (PMA), dipropylene glycol n-propyl ether (DPnP), dipropylene glycol methyl ether (DPM) and mixtures thereof.

10. The air freshening formulation of claim 9 wherein the co-solvent is selected from the group consisting of: dipropylene glycol methyl ether acetate (DPMA), dipropylene glycol n-propyl ether (DPnP), dipropylene glycol methyl ether (DPM) and mixtures thereof.

11. The air freshening formulation of claim 1, wherein the co-solvent is selected from the group consisting of: ethylene glycol monopropyl ether, ethylene glycol monoisopropyl ether, ethylene glycol monobutyl ether, ethylene glycol monophenyl ether, ethylene glycol monobenzyl ether, diethylene glycol monomethyl ether, diethylene glycol monoethyl ether, and diethylene glycol mono-n-butyl ether and mixtures thereof.

12. The air freshening formulation of claim 11 wherein the cosolvent is selected from the group consisting of: ethylene glycol monopropyl ether, ethylene glycol monoisopropyl ether, ethylene glycol monobutyl ether, ethylene glycol monophenyl ether, ethylene glycol monobenzyl ether, and mixtures thereof.

13. The air freshening formulation according to claim 1 wherein the alcohol is ethanol and the co-solvent is dipropylene glycol n-propyl ether (DPnP).

14. The air freshening formulation according to claim 13 wherein the formulation comprises:
    a) water, 48-52% by weight;
    b) ethanol, 26-30% by weight;
    c) dipropylene glycol n-propyl ether (DPnP), 18-22% by weight; and
    d) a fragrance composition, 1-3% by weight.

15. The air freshening formulation according to claim 1, wherein the formulation further comprises a corrosion inhibitor.

16. The air freshening formulation according to claim 15 which comprises less than 0.5% by weight of the corrosion inhibitor.

17. The air freshening formulation according to claim 16 wherein the formulation consists of;
    a) water, 48-52% by weight;
    b) ethanol, 26-30% by weight;
    c) dipropylene glycol n-propyl ether (DPnP), 18-22% by weight;
    d) a fragrance composition, 1-3% by weight; and
    3) a corrosion inhibitor, <0.5% by weight.

18. The air freshening formulation according to claim 1 wherein the propellant present in the pressurizable canister is a compressed gas propellant.

19. The air freshening formulation according to claim 18 wherein the compressed gas propellant is selected from the group consisting of: air, nitrogen and carbon dioxide.

20. The air freshening formulation according to claim 1, wherein the canister is any one of: a steel canister, tin-plated steel canister and other corroding metal canister.

21. The air freshening formulation according to claim 1, wherein in the volume ratio of propellant to formulation is within the range of from 80:20 to 30:70.

22. The air freshening formulation according to claim 1, wherein the initial flow rate of the air freshening formulation dispensed as an aerosol from the pressurizable canister is between 0.5 and 3.0 grams per second.

23. The air freshening formulation according to claim 1, wherein an aerosol dispersed from the pressurizable canister has mean particle size of between 20 and 80 microns.

24. A method of dispensing the air freshening formulation according to claim 1 from the pressurizable canister, the method comprising the steps of:
    dispensing the air freshening formulation utilizing an automatic aerosol dispensing device which device dispenses the air freshening formulation from within the pressurizable canister.

25. A method of freshening the air, the method comprising the steps of:
    inserting into an automatic aerosol dispensing device an air freshening formulation according to claim 1, and, activating the device to dispense the air freshening formulation from within the pressurizable canister.

26. The air freshening formulation present within a pressurizable canister comprising a propellant according to claim 1, wherein when dispensed from the canister by an automatic aerosol dispenser having surfaces in the proximity thereof, the dispensed formulation exhibit reduced buildup on said surfaces.

* * * * *